(12) United States Patent
Grajales et al.

(10) Patent No.: US 6,930,608 B2
(45) Date of Patent: Aug. 16, 2005

(54) APPAREL HAVING MULTIPLE ALTERNATIVE SENSORS AND CORRESPONDING METHOD

(75) Inventors: Liliana Grajales, Bloomingdale, IL (US); John St. Peter, Elburn, IL (US); Bill Olson, Lake Villa, IL (US); Mark Allen Krizik, Lockport, IL (US); Andrew Skipor, West Chicago, IL (US)

(73) Assignee: Motorola, INC, Schaumburg, IL (US)

( * ) Notice: Subject to any disclaimer, the term of this patent is extended or adjusted under 35 U.S.C. 154(b) by 169 days.

(21) Appl. No.: 10/145,600

(22) Filed: May 14, 2002

(65) Prior Publication Data
US 2003/0214408 A1 Nov. 20, 2003

(51) Int. Cl.[7] ............................................... G08B 23/00
(52) U.S. Cl. ................ 340/573.5; 340/573.6; 340/521; 128/206.21; 128/202.19
(58) Field of Search .................. 340/573.5, 573.6, 340/573.7, 573.1, 521, 523, 525; 128/204.23, 204.22, 206.21, 205.23, 202.19, 202.21, 201.29

(56) References Cited

U.S. PATENT DOCUMENTS

| | | | |
|---|---|---|---|
| 4,494,553 A | 1/1985 | Sciarra et al. | |
| 4,960,118 A * | 10/1990 | Pennock | ................ 128/200.24 |
| 5,622,180 A | 4/1997 | Tammi et al. | |
| 5,749,365 A | 5/1998 | Magill | |
| 5,973,602 A | 10/1999 | Cole, III et al. | |
| 6,032,530 A | 3/2000 | Hock | |
| 6,080,690 A | 6/2000 | Lebby et al. | |
| 6,121,881 A | 9/2000 | Bieback et al. | |
| 6,199,550 B1 * | 3/2001 | Wiesmann et al. | .... 128/204.23 |
| 6,289,238 B1 * | 9/2001 | Besson et al. | .............. 600/509 |
| 6,349,201 B1 | 2/2002 | Ford | |
| 6,388,422 B1 * | 5/2002 | Lew | ........................... 320/107 |
| 6,525,662 B1 | 2/2003 | Ford | |
| 6,551,252 B2 * | 4/2003 | Sackner et al. | ............. 600/536 |
| 6,595,918 B2 * | 7/2003 | Gopinathan et al. | ........ 600/300 |
| 6,606,993 B1 * | 8/2003 | Wiesmann et al. | .... 128/204.23 |

* cited by examiner

Primary Examiner—Jeffery Hofsass
Assistant Examiner—Daniel Previl
(74) Attorney, Agent, or Firm—Fitch, Even, Tabin & Flannery (57) ABSTRACT

One or more items of apparel have a plurality of sensors (10, 11, and 12) disposed therein (either permanently or temporarily). These sensors sense physical states of the individual wearing the items of apparel and/or of the local environment. In one embodiment, multiple sensors sense, in alternative ways, a parameter that corresponds to a physical state of interest. Information from these alternative sensing approaches is co-processed to yield a resultant parameter value that can be used in various ways. In one embodiment, the parameter value is locally or remotely displayed. In one embodiment, the parameter value is used in comparison against risk thresholds to ascertain a degree of risk to the individual.

30 Claims, 4 Drawing Sheets

APPAREL HAVING MULTIPLE ALTERNATIVE SENSORS AND CORRESPONDING METHOD

TECHNICAL FIELD

This invention relates generally to human and/or environmental monitoring and more particularly to such sensors as carried about by a person.

BACKGROUND

Various sensors are known in the art. Some sensors are useful to evaluate the physiological state of a human subject. For example, sensors exist that can monitor pulse (heart rate), respiration rate, blood oxygen, blood pressure, body temperature, and ambulatory electrocardiogram, to name a few. Typically, such sensors must be in contact with the skin of the subject in order to provide reliable measurements of the desired physical parameter. Often times the subject's skin must be prepared in a specific way to interface with the sensor. Other times a dielectric cream or conductive gel must be utilized to assure a satisfactory coupling. Most such sensors are designed for use in a controlled environment, such as a doctor's office or a hospital facility. A few sensors of these types are designed for more portable use. With respect to the latter, data is typically collected during one period of time and then batch evaluated at a later time by skilled technicians and/or medical personnel.

Other sensors are useful to evaluate the local environment. For example, sensors exist that can monitor for ambient temperature, carbon monoxide levels, explosive gases, harmful bacteria and/or viruses, hazardous chemicals, and so forth. Many such sensors are permanently installed to effect constant monitoring of a specific area. Other sensors are provided in a hand-held form factor to facilitate moving the sensor mechanism as needed.

Many occupations and even some hobby interests have a concomitant risk of exposure to potentially dangerous environmental conditions and/or to circumstances that otherwise present a physiological risk to a given subject. For example, fire fighters, strategic weapons and tactics squads, industrial maintenance workers and many others face the risk of working environments where the characteristics of that environment are either dangerous in and of themselves or where the working context is one that presents significant physiological challenges to the subject. Fire fighters, for example, face the risk of encountering high heat, leaking natural gas, chemical spills, and dangerous gases such as carbon monoxide. For these and a variety of other reasons, fire fighters also typically work in a high stress environment. Significant and repeated stress is known to raise dangerous health concerns, including heart attacks and other harmful circulatory events.

It would be beneficial if subjects such as fire fighters could readily and easily monitor their working environment for potentially dangerous conditions. It would also be beneficial if such subjects could also monitor their own relevant physiological state and thereby improve their likelihood of avoiding a sudden decrease in their working efficiency and/or personal safety. For a few individuals, such as astronauts, relevant physiological sensors can be and are attached in ordinary known ways to the skin of the astronaut to facilitate monitoring of their physical state. As noted, however, considerable preparation is required to properly prepare an individual in this way. For most individuals who could benefit from such monitoring, such as fire fighters, their mode of operation simply doesn't conveniently allow for sufficient time, personnel, or training to permit such practices. For the majority of individuals, little or no additional time can be allotted to the positioning and attachment of one or more sensors, notwithstanding the potential benefits of such monitoring.

BRIEF DESCRIPTION OF THE DRAWINGS

The above needs are at least partially met through provision of apparel having multiple alternative sensors and a corresponding method described in the following detailed description, particularly when studied in conjunction with the drawings, wherein.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present invention. Also, common but well-understood elements that are useful or necessary in a commercially feasible embodiment are typically not depicted in order to facilitate a less obstructed view of these various embodiments of the present invention.

DETAILED DESCRIPTION

Generally speaking, pursuant to these various embodiments, one or more items of apparel have a plurality of sensors disposed collectively therein. At least two of the sensors sense, in alternative ways, a parameter that corresponds to a given physical state. In one embodiment, at least some of the sensors are removably disposed, such that the sensor can be removed to facilitate laundering of the item of apparel or installation in a different item of apparel. In one embodiment, at least one of the sensors is disposed without contacting the skin of the wearer. By leveraging sensor fusion and monitoring a physical state parameter in alternative ways, the error often associated with such non-skin contact monitoring for a given sensor can be significantly mitigated.

The sensors themselves can, if desired, be permanently affixed within the apparel items (as used herein, "within" includes disposing a sensor on an inner surface of an item of apparel, on an outer surface of an item of apparel, and between inner and outer surfaces of an item of apparel). This can be done, for example, by sewing or by use of appropriate adhesives, rivets, clips, and so forth. Such an approach, of course, raises laundering concerns if the item of apparel requires frequent cleaning and if the sensor device is susceptible to the laundering agent. Steps can be taken to protect the sensor through use of impermeable membranes that encapsulate the sensor device, but such protective measures may be expected in many instances to interfere with proper operation of the sensor itself. A preferred embodiment, at least for most items of apparel, provides for non-permanent installation of the sensors. This can be accomplished in many ways, including but not limited to sensor pockets, hook-and-loop attachment mechanisms, zippers, snaps, and so forth. So configured, the sensors can be readily removed from the item of apparel to permit ordinary cleaning of the item without risk to the sensors themselves.

Depending upon the embodiment, wearable local displays can be provided to allow the wearer to view information pertaining to the monitored parameter(s). Also, in various embodiments, wireless communications are utilized to network at least some of the plurality of sensors and/or to network the sensors to another radio platform (such as a hand held two-way radio or vehicle mounted land mobile radio).

Figure 1:
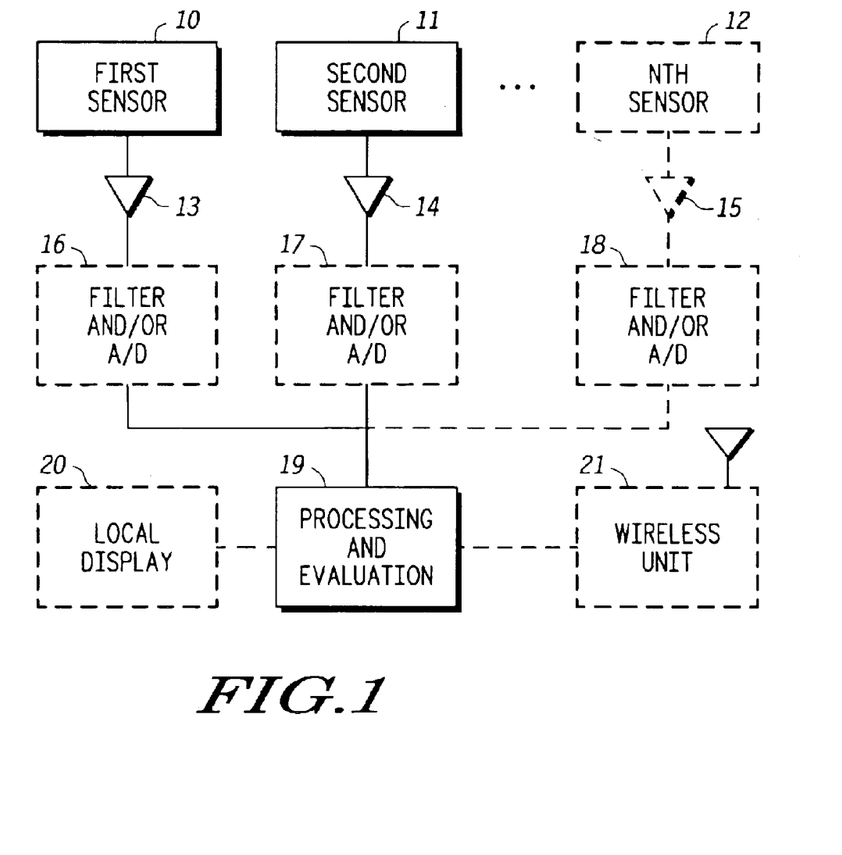
FIG. 1 comprises a block diagram as configured in accordance with an embodiment of the invention.

Referring now to FIG. 1, pursuant to these embodiments a plurality of sensors are provided. This includes a first sensor 10, a second sensor 12, and as many additional sensors (represented here by an Nth sensor 12) as may be appropriate to a given application. As will be described in more detail below, these sensors are disposed within one or more items of apparel. (As used herein, "an item of apparel" or "items of apparel" refers generally to all manner of clothing and corresponding accessories, such as but not limited to shirts, coats and jackets, vests, pants, shorts, socks and gloves, shoes and boots, underclothing, and hats, helmets, or other headgear. These expressions can also refer to accessories such as neckties and scarves, sweatbands of various kinds, jewelry and wristwatches, and so forth.)

In general, most and/or all of these sensors will be located proximal to an individual who is wearing the apparel in question, but they will not ordinarily have firm and consistent contact with the individual's skin. Depending upon the sensor and the item of clothing, some sensors will likely never have direct contact with the skin of an individual. On the one hand, this offers a significant benefit in that no special preparation or care need be taken by the individual, nor is significant training required. The individual simply puts their clothing on in an ordinary fashion and the sensors will automatically be appropriately generally positioned with respect to the parameter to be monitored.

On the other hand, because little or no skin contact is expected or required, any given sensor at any given moment may be providing false and/or noisy data. In particular, signal artifacts that are due to motion of the individual should be expected. Accurate results are nevertheless attainable through use of multiple sensors, and especially wherein these sensors utilize alternative ways to sense a given parameter of interest. (For example, different sensors can alternatively sense information as a function of at least any of sound, ultrasonic sound, voltage potential, infrared, ultraviolet, temperature, pressure, radar, electromagnetism, and laser light.) Such sensor fusion permits useful information to be ascertained notwithstanding the absence of skin contact and/or exact placement of all sensors with respect to an individual's body.

Some specific illustrative examples of this sensor fusion approach are:

EXAMPLE 1

The pulse of an individual can be ascertained in a variety of ways. A first sensor 10 can comprise a sound transducer (such as an appropriate microphone) positioned proximal the chest of the individual. So positioned, the heartbeat can be detected and corresponding temporal calculations made to derive a pulse rate. A second sensor 11 can comprise a magnetic body sensor positioned, for example, at the chest or shoulder of the individual. Such a sensor, typically comprising a magnetic wire loop that encircles the targeted body portion, is responsive to the body's own magnetic field and is sufficiently sensitive as to be able to again detect the individual's pulse. A third sensor 12 can comprise a radio frequency sensor located proximal the chest of the individual. Radio frequency reflectivity and impedance will vary with the pulse of the individual. Therefore, again, the pulse rate of the individual can be ascertained in this fashion. Under ordinary circumstances, any of these three approaches would suffice to obtain an accurate reading of the individual's pulse rate. By locating these sensors with normal apparel items, however, considerable noise and varying signal strength can and should be expected. By using multiple sensors, and particularly by using a plurality of sensors that use differing approaches to measuring the physical state parameter in question, the resultant data can be processed to yield a substantially valid parameter value at least most of the time.

EXAMPLE 2

The same sensors as are used in Example 1 above can also be used to provide a measurement of the individual's rate of respiration. In particular, the first sensor 10 (a sound transducer) can detect the inward and outward sounds of breathing, the second sensor 11 (the magnetic body sensor) can detect magnetic field variations that are owing to respiration, and the third sensor 12 (the radio frequency sensor) can detect reflection and impedance variations that track movement of the individual's diaphragm. Again, such signals are combinable (or fusible) to yield a composite parameter value that features acceptable levels of accuracy.

EXAMPLE 3

The body temperature of an individual can be monitored as well by three different sensors. The first sensor 10 can be either of a resistance temperature detector (RTD) or thermistor disposed, for example, at the cuff or armpit area of the individual. So positioned the sensor will provide an output that varies with the individual's body temperature. The second sensor 11 can be an infrared sensor located, for example, proximal the chest of the individual. This sensor 11 will, again, provide a signal that varies with the body temperature of the individual. And the third sensor 12 can be a magneto-elastic sensor located, for example, proximal the neck or armpit of the user. (Magneto-elastic sensors typically include two coils, the first being a pickup coil and the second being an interrogation coil, wherein the resonant frequency of the sensor shifts with respect temperature due to elastic deformation of the constituent parts. Such coils are typically formed of materials such as $Fe_4ONi_{38}Mo_4B_{18}$ and $Fe_{81}B_{13}Si_{3.5}C_2$.) These sensors each detect body temperature using differing and alternative sensor mechanisms. And again, the sensed result for any given sensor can be considered somewhat suspect at any given moment in time due to the issues noted above. Upon fusing the sensor results, however, a relatively accurate reading can be obtained at least most of the time.

The specific individual sensor technologies noted above are each understood in the art. Hence, additional detailed description will not be provided here for the sake of brevity and focus. It should be noted, however, that the examples given are intended to be illustrative only, as the benefits of these embodiments are readily realized for a variety of physical state parameters with a wide variety of sensor mechanisms. For example, sensors useful to monitor an individual's blood oxygen, blood pressure, vertical bearing, movement, and ambulatory EKG can all be used with similar beneficial results.

In addition, the examples provided above are directed to sensors intended to monitor a physical state of the individual themselves. If desired, sensors can also be provided that serve to monitor specific aspects of the environment local to the individual. For example, sensors that would serve to detect heat, smoke, carbon monoxide, carbon dioxide, explosive gases, toxic gases, biohazards such as specific bacteria, fungi, and viruses, and hazardous chemicals could all be disposed within the individual's apparel to support automatic environmental monitoring of such parameters.

For many applications it is likely that the resultant signal from such sensors will be relatively small in amplitude. To mitigate such circumstances and to render the sensor signals useful for processing, a high gain amplifier 13, 14, and 15 can be utilized to amplify the corresponding sensor signals. Next, and optionally, the amplified signals can be filtered and/or converted to digital form prior to being provided to a processing and evaluation unit 19. If such filtering and/or converting is not done by separate dedicated units 16, 17, and 18, then in most cases such functionality should usually be provided in the processing and evaluation unit 19 itself.

The processing and evaluation unit 19 will typically comprise a programmable platform, such as a microprocessor, having appropriate logic and storage capability along with input and output capabilities that are appropriate to the given application. More specifically, the processing and evaluation unit 19 serves to receive the sensor inputs from the various sensors and fuse those corresponding signals in a temporally consistent manner. The window of time over which the processing and evaluation unit 19 fuses the sampled information will likely vary, depending upon the physical state parameter being monitored and the specific sensor technologies themselves. In general, however, the processing and evaluation unit 19 should process the available information in sufficient time to consider the end result to be substantially real time.

Fusing data from multiple sensors can be done in a variety of ways. For example, the results of each can simply be normalized and then averaged to achieve a resultant parameter value. As another example, the results of each sensor can be weighted after normalization to pad the result in favor of sensor technologies known to be relatively more accurate under most circumstances and/or to diminish the contribution of a sensor technology known to be relatively inaccurate under many ordinary operating circumstances. As another example, the rate of change, or time derivative, of each sensor signal can be used to assess the accuracy of each signal, and only those signals whose rate of change occurs within previously set limits need be utilized. For example, an individual's body temperature rate of change is limited to some extent by their body mass. If an infrared temperature sensor signal monitoring a person's body temperature displays an unreasonably fast rate of change, the signal from that sensor can be discarded. Conversely, the signals from sensors that compare favorably with a rate of change limit can be used accordingly.

Figure 8:
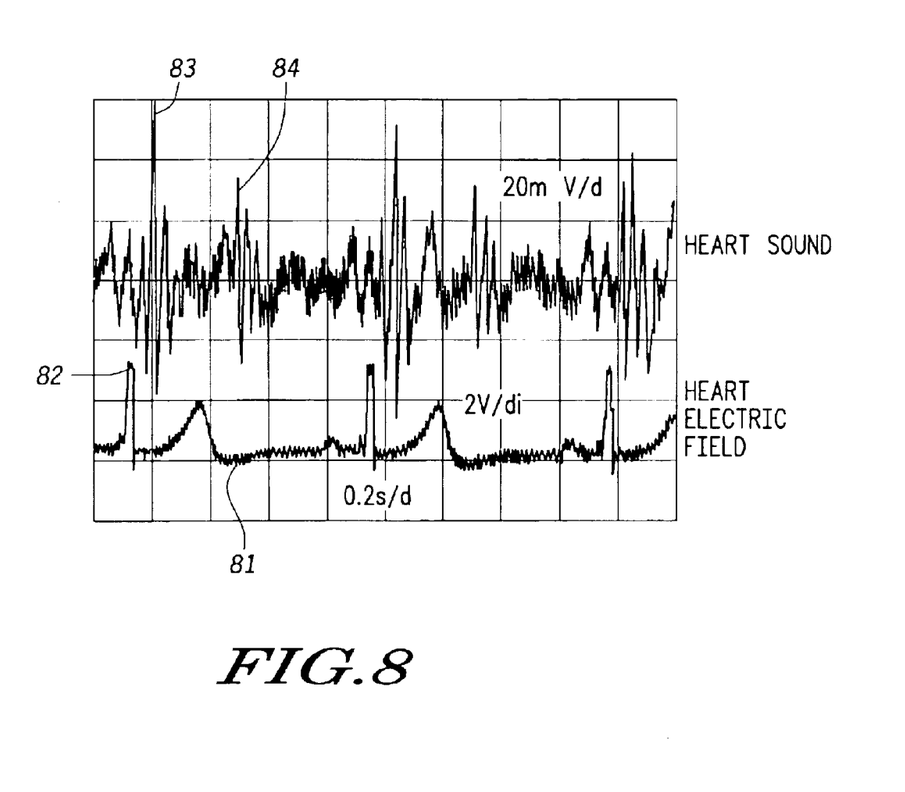
FIG. 8 comprises a graph depicting various monitorable parameters of a heart.

Yet another approach would provide circumstantial sensors that detect circumstances and/or conditions that can lead to inaccurate results from one or more of the sensors (for example, an accelerometer could be used to sense sudden movement of the individual, such that information from a sensor that is known to more likely produce erroneous results during such intervals is dynamically downwardly weighted or discarded for the duration). Yet another approach can be the use of a signal, or part of a signal, to trigger, warn, or otherwise influence another sensor. For example, and referring momentarily to FIG. 8, when measuring the heart's electrical signal 81 with ECG techniques using skin-contact electrodes or high impedance remote probes, the ECG QR rising voltage signal 82 ordinarily occurs earlier than heart valve sounds 83 and 84. Thus, a sound transducer could be synchronized to begin sensing for heart valve sounds only following detection of an ECG QR signal. Such synchronization between one or more sensors can be similarly used to reduce the noise of various other vital sign measurements.

Still another approach can combine any of the above with weighting factors that represent historical information for this individual. Such an approach can likely reduce artifacts that constitute significant and sudden transients from inappropriately influencing the fused result. There are other ways as well, of course, that the sensor signal information can be appropriately processed to yield a parameter value that is of acceptable veracity.

If desired, the processing and evaluation unit 19 can also evaluate the resultant parameter value(s) to detect potentially injurious physical states. For example, a threshold pulse rate can be stored within the processing and evaluation unit 19. If and when the monitored pulse rate exceeds the threshold pulse rate (as a single occurrence or, alternatively, following a sufficient number of sequential confirming events as desired to eliminate at least some false positives), the processing and evaluation unit 19 can, for example, provide an alarm such as an audible signal. The thresholds used for such purposes can be universal or tailored to a specific individual (taking into account any of the individual's age, physical fitness, and the like) depending upon the needs of the application and the desires of the individual.

If desired, a local display 20 can be provided within the clothing of the individual. This local display 20 can be appropriate coupled to the processing and evaluation unit 19 to permit presentation on the display of various items of desired information. For example, in one embodiment, the processing and evaluation unit 19 can cause local display of the corresponding individual sensor outputs and/or the fused informational result. When the processing and evaluation 19 provides local detecting of potentially dangerous circumstances, then of course the display 20 can also be used to display information regarding such circumstances (including either objective information regarding the corresponding physical state and/or advice, instructions, or orders regarding actions the individual should now implement).

In another embodiment, the processing and evaluation unit 19 can couple to a wireless unit 21. Depending upon the needs of the specific embodiment, this wireless unit 21 can be a transmitter, a receiver, or a transceiver. When the wireless unit 21 comprises a device capable of transmission, the processing and evaluation unit 19 can use the wireless unit 21 to transmit the fused sensor information and/or the results of any local threat evaluation. When the wireless unit 21 comprises a device capable of reception, the processing and evaluation unit 19 can use the wireless unit 21 to receive instructions and orders to either be implemented by the processing and evaluation unit 19 and/or the individual. When the wireless unit 21 comprises a transceiver, if desired, the evaluation functionality described above can be moved to a remote location (where, perhaps, considerably greater computational power may be available to effect rapid and accurate processing and evaluation of the sensor information). The processing and evaluation unit 19 can then receive the results of the remote evaluation and utilize the information accordingly. Additional information and description regarding various ways to leverage the availability of a wireless unit 21 are presented below where relevant.

Figure 2:
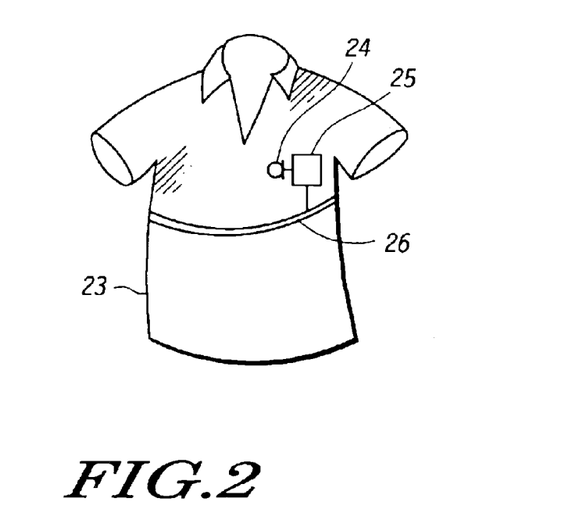
FIG. 2 comprises a front elevational view as configured in accordance with an embodiment of the invention.

FIG. 2 depicts one simple embodiment wherein a torso enveloping garment (such as a shirt) 23 has a first sensor 24 comprising a sound transducer affixed within the garment 23 proximal the chest and preferably proximal the heart and a second sensor 26 comprising a magnetic wire loop style sensor 26 disposed to substantially circumscribe, in this embodiment, the individual's chest. In this embodiment, the first sensor 24 can be placed, for example, within an inner pocket (not shown) provided therefore, and the second sensor 26 can be retained in place, for example, through use of hooks-and-loops fasteners. So configured, both sensors can be readily removed to permit cleaning of the garment 23.

Both sensors 24 and 26 are coupled to a processing and evaluation unit 25 (signal amplification, filtering, and/or conversion from the analog to digital domain can be accomplished at the processing and evaluation unit 25, at the sensors 24 and 26 themselves, or via an intermediary device or devices as described earlier). As with the sensors, the processing and evaluation unit 25 is also only temporarily installed in the garment 23 via, for example, another interior pocket (not shown).

So configured, the user need only don the garment 23 in an ordinary fashion. The devices can then be switched into an active state by the user through manipulation of an appropriate switch. If desired, activation can be done automatically. One way to achieve this would be to provide a motion sensor that would in turn activate the sensors and processing circuitry upon sensing movement of the garment 23. Another way to achieve automatic activation would be to provide a radio frequency tag that, when strobed by an activation signal (as might be provided, for example, at the exit to a fire station) would in turn provide an activation signal to the remaining circuitry. Yet another approach would be to provide a portable power supply (through use of batteries) sufficient to maintain the sensors and processing unit in an energized state through a given work period (such as, for example, a single day); with this approach, the depicted sensors and attendant circuitry would simply be in a state of activation at all times.

These same kinds of relatively simple installation and positioning choices can be effected with other items of apparel and sensors as noted earlier. In most cases the sensors can be readily installed in a temporary fashion and yet still suffice to provide useful data regarding the physical state parameter in question (at least to the extent that the data can be useful when processed in conjunction with the data from other sensors as well).

Figure 3:
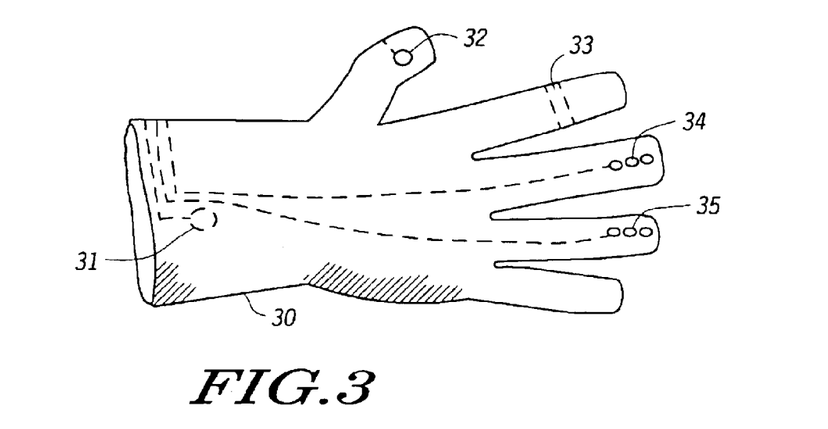
FIG. 3 comprises a palm-side view of a glove as configured in accordance with an embodiment of the invention.
Figure 4:
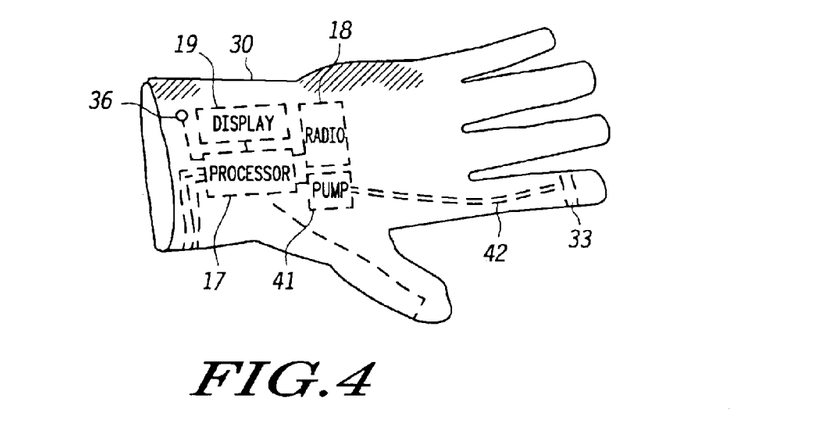
FIG. 4 comprises a knuckle-side view of the glove as configured in accordance with an embodiment of the invention.

FIGS. 3 and 4 depict another embodiment wherein the relevant circuitry is more permanently installed. In this embodiment, a glove 30 has a first sensor 31 located on the palm side of the glove 30 that comprises, for example, a thermistor or an infrared temperature sensor to ascertain the temperature of the wearer. Another sensor 36 comprising, for example, an optical sensor, is located on a part of the glove 30 that will tend to be positioned over a prominent vein or artery. In this embodiment, this sensor 36 is located so as to be positioned on the backside of the hand, near the wrist, proximal to a relatively large vein. Such a sensor 36 provides data that is useful in determining information regarding the pulse rate as well as blood oxygen levels of the wearer. A third sensor 32 is located on the thumb (or, in an alternative embodiment, on the index finger) of the glove 30 and comprises, for example, an optical or electrical sensor that can again measure the heart rate and blood oxygen as well. (In this embodiment two sensors 36 and 32 are provided to monitor common parameters as both sensors are subject to motion artifact at any given moment. Also, since optical triggers tend to require relatively significant quantities of power, optical sensors such as these can be triggered on and off as appropriate to provide for sensor readings only during useful monitoring windows where power source limitations are of concern)

Another sensor 33 comprises an inflatable ring (which is selectively inflatable and deflatable by a small pump 41 that is coupled to the inflatable ring 33 by a small pneumatic pathway 42) and a pressure sensor. This sensor 33 provides data that is useful when seeking to measure the blood pressure and heart rate of the wearer. Lastly, one or more sensors 34 and 35 can be provided on the distal ends of the glove's fingertips. These sensors 34 and 35 serve to monitor physical state parameters external to the wearer of the glove 30. For example, these sensors 34 and 35 could include a temperature sensitive sensor to detect external heat (especially when the glove is used to touch a door or other obstacle to ascertain whether a dangerous conflagration is present on the other side of the obstacle), a pressure sensor, a carbon monoxide sensor, an oxygen sensor, and so forth.

In addition to the sensors noted above, of course, a wide variety of other sensors could be so employed to monitor the individual and/or the local environment.

In this embodiment, all of these sensors are substantially permanently affixed within the glove 30. Care would therefore be needed when cleaning such an item of apparel. If desired, the sensors and other related circuitry could be made removable. Accommodating such provisions, however, may likely interfere with the dexterity of the wearer's hand when wearing the glove.

All of these sensors couple appropriately to a processing unit 17 which is located, in this embodiment, on the side of the glove opposite the palm side as depicted in FIG. 4. The processing unit 17 functions as described earlier, though in this case the processing unit 17 may not engage in evaluation of the data. In this embodiment, however, the processing unit 17 can couple to a small wireless unit 18 comprising, in this example, a very short range radio frequency transceiver (such as one finds in a so-called personal area network). So configured, the processing unit 17 can transmit the sensor data (perhaps as already subjected to gain, filtering, and even digitization as desired) to another processing unit located elsewhere in the apparel of the wearer. This latter processing unit could then combine the sensor readings of the glove sensors with information from other sensors to thereby practice the teachings made herein.

A display 19 is also provided in this embodiment. The display 19 could be, for example, a small liquid crystal display. Information from the processing unit 17 itself could be displayed, or, the processing unit 17 could cause the display of parameter readings and/or other information or instructions as received via the wireless unit 18.

So configured, a variety of physical state parameters can again be readily monitored without requiring the wearer to take any particularly time consuming actions. Instead, for the most part, the individual simply dons their items of apparel in a substantially ordinary fashion and nevertheless receives the benefits of such sensing, monitoring, and processing.

Figure 5:
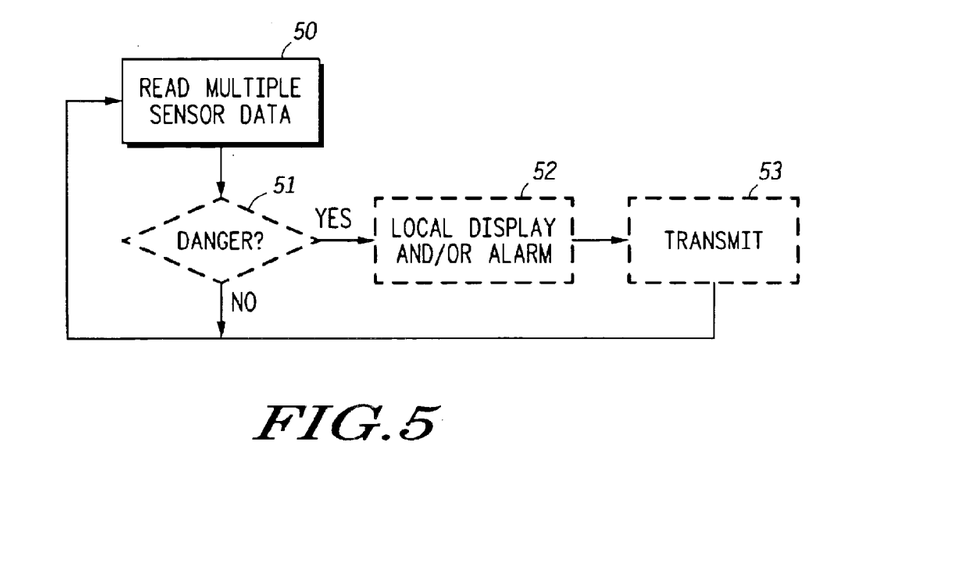
FIG. 5 comprises a flow diagram as configured in accordance with an embodiment of the invention.

Referring now to FIG. 5, as noted earlier, these embodiments provide for the reading 50 of sensor data from a plurality of sensors and particularly from a plurality of sensors that sense, in alternative ways, one or more parameters that correspond to various physical states of interest. In one embodiment, these sensor readings can be evaluated to ascertain a likely reading of the physical state and then compare that reading against a threshold to determine 51 whether the individual being monitored faces a potentially dangerous circumstance. For example, if an individual's pulse rate is presently exceeding a dangerous threshold, that circumstance can lead to a determination that the individual faces heightened risk (i.e., in this case, of suffering a heart attack or other related circulation anomaly). Upon determining that such a risk exists, if desired and presuming the availability of a local display, information regarding the parameter in question and/or a warning statement can be provided 52 (either with or without an audible alarm sound to alert the individual to consult the display and take appropriate action). Also depending upon the physical embodiment, if a wireless transmission mechanism is available, the raw sensor readings and/or parameter readings based upon the sensor readings and/or warnings information can be transmitted to a location remote from the user to facilitate remote monitoring and/or decision making.

Figure 6:
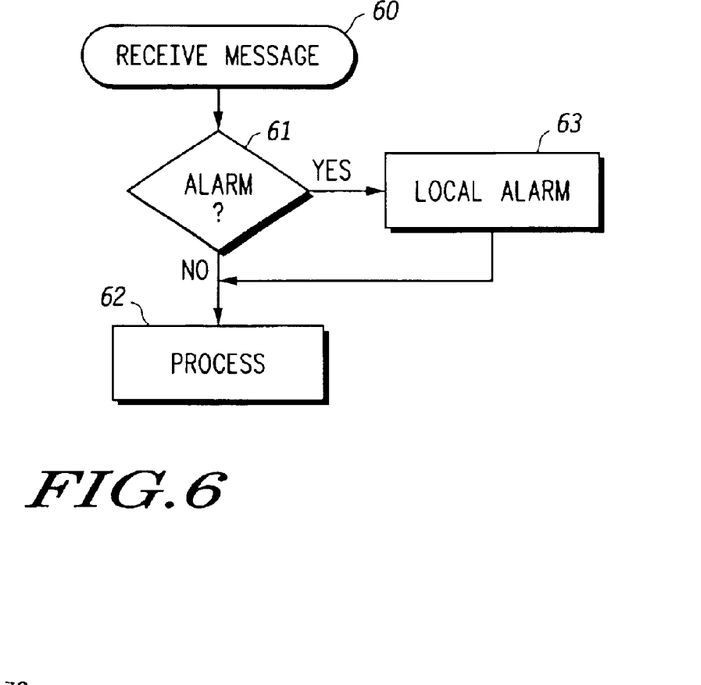
FIG. 6 comprises a flow diagram as configured in accordance with an embodiment of the invention.

As noted above, in some embodiments the individual wearing the sensors may not have local sensor data evaluation processing capability on-board. As also noted above, in such a case, the sensor data can be transmitted to a remote location where resources are available to support such evaluation. In such a case, and referring now to FIG. 6, when the local wireless unit receives 60 a message, the receiving unit case ascertain 61 whether an alarm condition exists. When true, a local alarm 63 can be provided followed by whatever additional processing 62 is appropriate to the given application. Also, as noted above with respect to FIG. 5, the received message can also contain specific instructions intended for the person wearing the items of apparel. In such a case, in addition to sounding the alarm, such instructions can be presented to the individual using a display, speaker, or other transducer as is appropriate to the form of the message.

Figure 7:
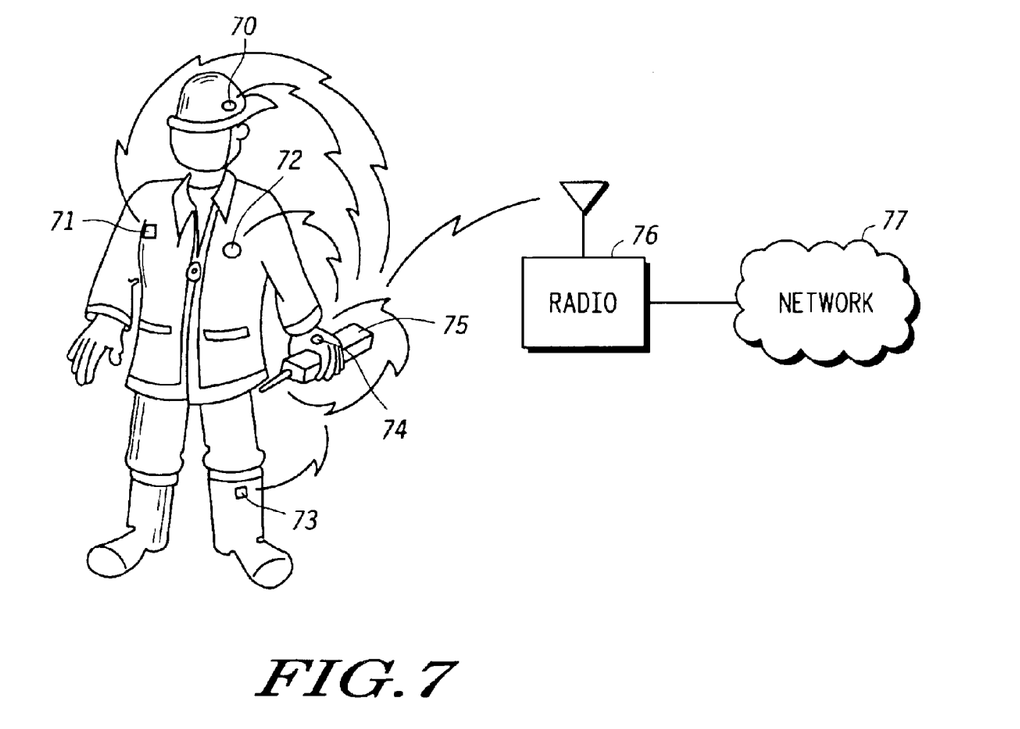
FIG. 7 comprises a diagram as configured in accordance with yet another embodiment of the invention.

Referring now to FIG. 7, it should be clear that an individual, such as a fire fighter, can position a plurality of sensors about their body by simply donning items of apparel that have the sensors pre-positioned therein. For example, a first sensor 70 could be positioned in a helmet, a second sensor 71 could be positioned in the armpit of a coat, a third sensor 72 could be positioned over the chest in the coat, a fourth sensor 73 could be positioned in a boot, and a fourth sensor 74 could be positioned in a glove. Information from these sensors could then be processed in a handheld two-way radio 75 that includes an appropriate transceiver (such as a personal area network transceiver) where the resultant parameters are then evaluated and risks of various kinds assessed. Corresponding information could then be transmitted by the two-way radio 75 (using, for example, ordinary transmission frequencies, signaling protocols, and modulation) to another radio unit 76 (such as might be mounted in a nearby vehicle or as provided in a distant communications facility such as a public safety dispatch communications center). The latter could, if desired, then be coupled to a network 77 such as, for example, a local area network or the Internet such that the information would be more widely available.

So configured, processing of the sensor data, evaluation thereof, issuance of threat warnings, and monitoring of any of the above can be distributed as is desired and convenient and as might be appropriate to a given application. For example, any of these processing steps could occur at one of the sensor locations, at a stand-alone processing and evaluation unit located elsewhere in the items of apparel, at the two-way radio, at a remote radio site, or at any other site having access via the network.

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept.

We claim:

1. An apparatus comprising:
   at least one item of apparel;
   a plurality of sensors disposed within the at least one item of apparel, wherein at least two of the plurality of sensors each sense, in alternative ways, a same parameter that corresponds to a given physical state.

2. The apparatus of claim 1 wherein the at least two of the plurality of sensors are disposed within one of the at least one item of apparel.

3. The apparatus of claim 1 wherein the at least one item of apparel comprises at least one of headgear, a torso covering, a glove, footwear, pants, a dress, an apron, a belt, suspenders, and an undergarment.

4. The apparatus of claim 1 wherein at least one of the plurality of sensors is readily removable from the at least one item of apparel such that the at least one item of apparel can be laundered without the at least one of the plurality of sensors.

5. The apparatus of claim 1 wherein the given physical state comprises at least one of human blood pressure, pulse rate, temperature, respiration rate, blood oxygen, movement, and vertical bearing.

6. The apparatus of claim 1 wherein the given physical state comprises at least one of environmental temperature and environmental content.

7. The apparatus of claim 6 wherein the environmental content includes at least one of carbon monoxide, carbon dioxide, toxic gases, explosive gases, and biohazards.

8. The apparatus of claim 1 wherein at least some of the plurality of sensors sense information as a function of at least one of sound, ultrasonic sound, voltage potential, infrared, ultraviolet, temperature, and pressure, radar, electromagnetism, and laser light.

9. The apparatus of claim 1 and further comprising a radio transmitter operably coupled to at least some of the plurality of sensors, wherein the radio transmitter is disposed within the at least one item of apparel.

10. The apparatus of claim 1 and further comprising a user interface having at least one of a display and an audible alarm operably coupled to at least one of the plurality of sensors, wherein the user interface is supported by the at least one item of apparel.

11. The apparatus of claim 1 and further comprising a processing unit that is operably coupled to the at least two of the plurality of sensors and wherein the processing unit is disposed within the at least one item of apparel.

12. The apparatus of claim 11 wherein the processing unit is operably coupled via a physical link to at least one of the at least two of the plurality of sensors.

13. The apparatus of claim 11 wherein the processing unit is operably coupled via a wireless link to at least one of the at least two of the plurality of sensors.

14. A method comprising:
disposing a plurality of sensors within apparel as worn by an individual, wherein the plurality of sensors includes at least two sensors that each differently senses a same given physical state;
processing information from a plurality of the at least two sensors to develop information regarding the given physical state.

15. The method of claim 14 wherein including at least two sensors that each differently senses a given physical state includes including at least two sensors that each differently senses a given physical state using alternative sensing techniques.

16. The method of claim 15 wherein disposing a plurality of sensors within apparel as worn by an individual, wherein the plurality of sensors includes at least two sensors that each differently senses a given physical state includes disposing a plurality of sensors within apparel as worn by an individual, wherein the plurality of sensors includes at least two sensors that each differently senses a given physical state that comprises at least one of human blood pressure, human pulse rate, human temperature, human respiration rate, human blood oxygen, human vertical bearing, human movement, environmental temperature, environmental toxic gases, environmental explosive gases, environmental carbon monoxide, environmental carbon dioxide, and environmental biohazards.

17. The method of claim 15 wherein processing information from a plurality of the at least two sensors to develop information regarding the given physical state includes processing the information within the apparel.

18. The method of claim 17 and further comprising wirelessly transmitting at least some of the information.

19. The method of claim 18 wherein wirelessly transmitting includes wirelessly transmitting at least some of the information only a relatively short distance.

20. The method of claim 18 wherein wirelessly transmitting includes using at least one of infrared transmission and radio frequency transmission.

21. The method of claim 14 wherein processing information from a plurality of the at least two sensors to develop information regarding the given physical state includes using a profile of data that corresponds to an individual who is wearing the apparel.

22. The method of claim 14 and further comprising displaying at least a portion of the information proximal to the apparel.

23. The method of claim 14 wherein disposing a plurality of sensors within apparel as worn by an individual includes disposing a plurality of sensors within apparel as worn by an individual such that the plurality of sensors do not physically contact skin of the individual.

24. An article of apparel having:
multiple sensor means disposed in the article of apparel for sensing, in alternative ways, a same physical state;
processing means disposed in the article of apparel and being operably coupled to the multiple sensor means for processing signals from the multiple sensor means and for providing information regarding the physical state as a function of each of the multiple sensor means.

25. The article of apparel of claim 24 and further including transmission means for transmitting at least some of the information regarding the physical state.

26. The article of apparel of claim 24 and further including display means operably coupled to the processing means for displaying at least some of the information regarding the physical state.

27. The article of apparel of claim 24 wherein processing signals from the multiple sensor means further includes comparing sensing sensor information with at least one predetermined threshold.

28. The article of apparel of claim 27 wherein processing signals further includes providing an alarm when the sensor information exceeds the at least one predetermined threshold.

29. The article of apparel of claim 27 wherein processing signals further includes providing a display of information when the sensor information exceeds the at least one predetermined threshold.

30. The article of apparel of claim 24 and further comprising wireless transmission means for wirelessly transmitting at least some information that corresponds to the signals from the multiple sensor means.

* * * * *

UNITED STATES PATENT AND TRADEMARK OFFICE
CERTIFICATE OF CORRECTION

PATENT NO. : 6,930,608 B2
DATED : August 16, 2005
INVENTOR(S) : Grajales et al.

It is certified that error appears in the above-identified patent and that said Letters Patent is hereby corrected as shown below:

Title page,
Item [73], Assignee, change "INC" to -- Inc. --.

Column 11,
Line 14, delete "includes.".

Signed and Sealed this

Twenty-fourth Day of January, 2006

JON W. DUDAS
*Director of the United States Patent and Trademark Office*